US010271972B2

(12) United States Patent
Guler et al.

(10) Patent No.: US 10,271,972 B2
(45) Date of Patent: Apr. 30, 2019

(54) COVERED ENDOSCOPIC STENTS WITH ADHESION ELEMENTS

(71) Applicant: Boston Scientific Scimed Inc., Maple Grove, MN (US)

(72) Inventors: Ismail Guler, Maple Grove, MN (US); Allan Charles Shuros, St. Paul, MN (US); Eric A. Mokelke, Flagstaff, AZ (US); Adam David Grovender, Brooklyn Park, MN (US); Joel P. Grover, St. Paul, MN (US); Timothy Lawrence Rubesch, Blaine, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 384 days.

(21) Appl. No.: 14/668,179

(22) Filed: Mar. 25, 2015

(65) Prior Publication Data
US 2015/0282955 A1 Oct. 8, 2015

Related U.S. Application Data

(60) Provisional application No. 61/974,069, filed on Apr. 2, 2014.

(51) Int. Cl.
| A61F 2/848 | (2013.01) |
| A61F 2/82 | (2013.01) |
| B32B 37/12 | (2006.01) |
| B32B 37/24 | (2006.01) |
| A61F 2/00 | (2006.01) |
| A61F 2/86 | (2013.01) |
| A61F 2/07 | (2013.01) |
| A61F 2/90 | (2013.01) |

(52) U.S. Cl.
CPC .............. *A61F 2/82* (2013.01); *A61F 2/0077* (2013.01); *A61F 2/86* (2013.01); *B32B 37/12* (2013.01); *B32B 37/24* (2013.01); *A61F 2/07* (2013.01); *A61F 2/848* (2013.01); *A61F 2/90* (2013.01); *A61F 2210/0076* (2013.01); *A61F 2220/0008* (2013.01); *A61F 2230/0067* (2013.01); *A61F 2230/0091* (2013.01); *B32B 2535/00* (2013.01); *Y10T 156/10* (2015.01)

(58) Field of Classification Search
CPC ....................................................... A61F 2/848
See application file for complete search history.

(56) References Cited

U.S. PATENT DOCUMENTS

| 1,836,202 | A | * | 12/1931 | Teigeler | .................. | E03C 1/308 |
| | | | | | | 4/255.11 |
| 2003/0009213 | A1 | | 1/2003 | Yang | | |
| 2005/0255230 | A1 | | 11/2005 | Clerc et al. | | |

(Continued)

FOREIGN PATENT DOCUMENTS

JP    2011156083 A    8/2011
WO    9951165         10/1999

*Primary Examiner* — Jacqueline Woznicki
(74) *Attorney, Agent, or Firm* — Seager, Tufte & Wickhem, LLP

(57) ABSTRACT

An endoprosthesis includes a stent having an inner surface defining a lumen and an outer surface; and a polymeric cover on the outer surface of the stent. The polymeric cover includes a base and adhesion elements. When the endoprosthesis is expanded to the expanded state in a lumen defined by a vessel wall, the adhesion elements create an interlock between the vessel wall and the endoprosthesis.

19 Claims, 10 Drawing Sheets

(56) References Cited

U.S. PATENT DOCUMENTS

| | | |
|---|---|---|
| 2006/0193892 A1 | 8/2006 | Furst et al. |
| 2007/0276342 A1* | 11/2007 | Lin .................. A61F 2/0036 |
| | | 604/264 |
| 2008/0199506 A1 | 8/2008 | Horres et al. |
| 2009/0069904 A1 | 3/2009 | Picha |
| 2009/0187240 A1 | 7/2009 | Clerc et al. |
| 2010/0076555 A1 | 3/2010 | Marten et al. |
| 2011/0021965 A1 | 1/2011 | Karp et al. |
| 2012/0035715 A1 | 2/2012 | Robida et al. |
| 2013/0110255 A1 | 5/2013 | Picha et al. |
| 2013/0268063 A1 | 10/2013 | Firstenberg et al. |
| 2014/0277395 A1 | 9/2014 | Firstenberg et al. |
| 2014/0277442 A1 | 9/2014 | Seddon et al. |
| 2015/0051693 A1 | 2/2015 | Bertolino et al. |

\* cited by examiner

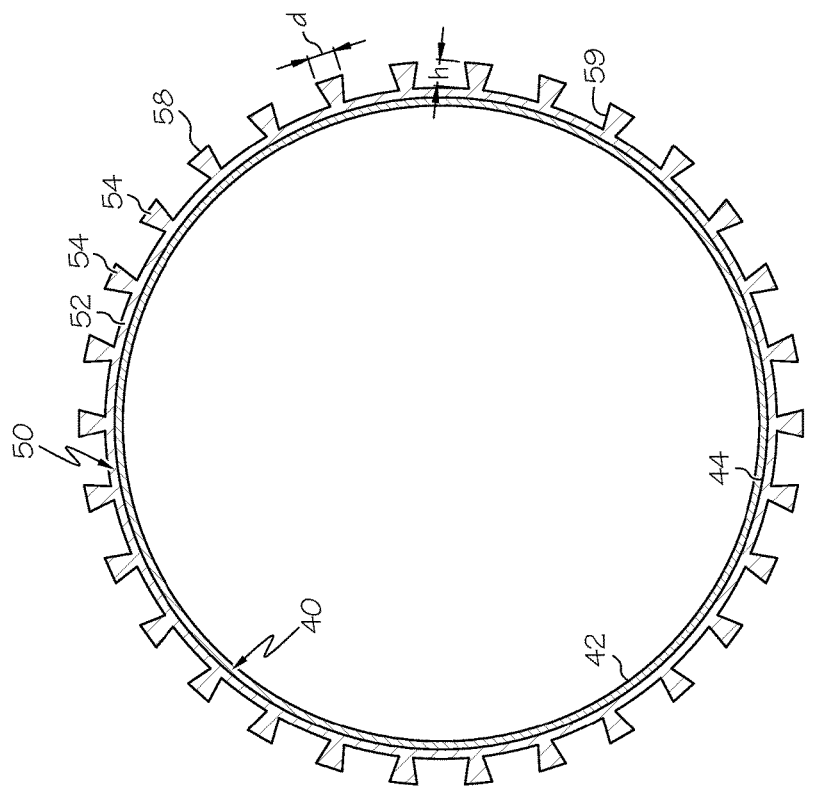
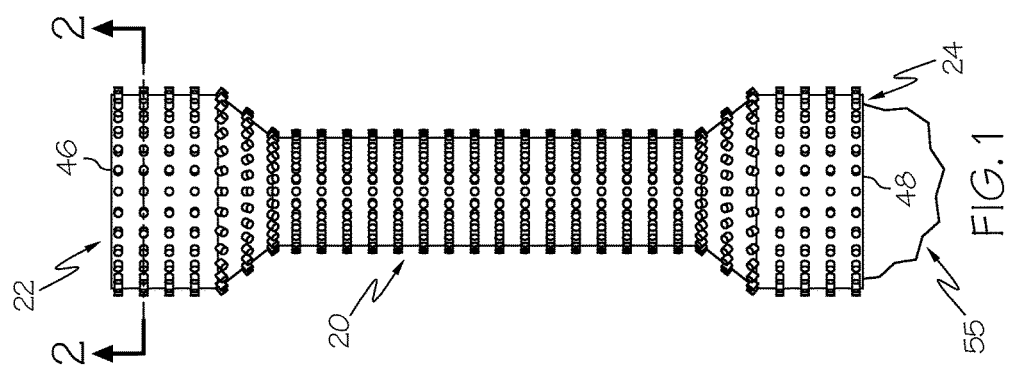

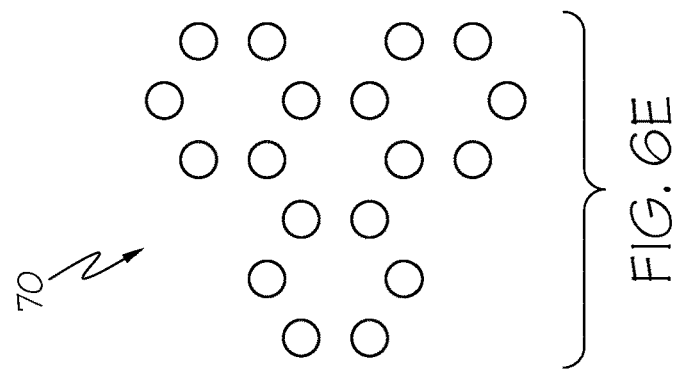
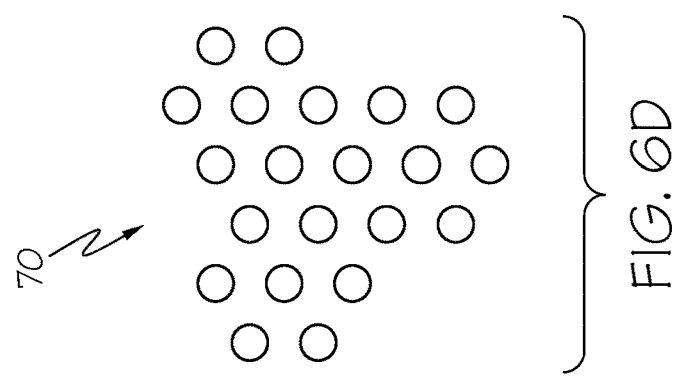
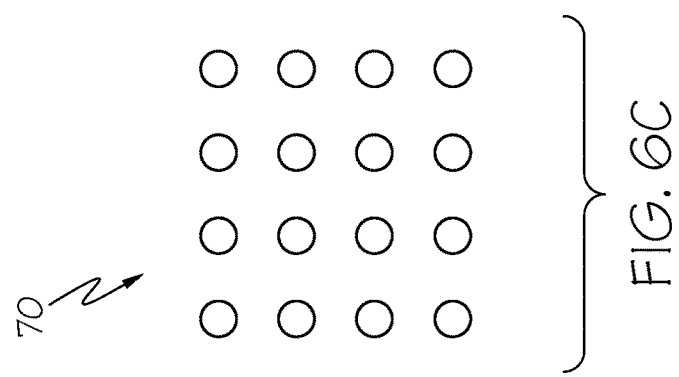

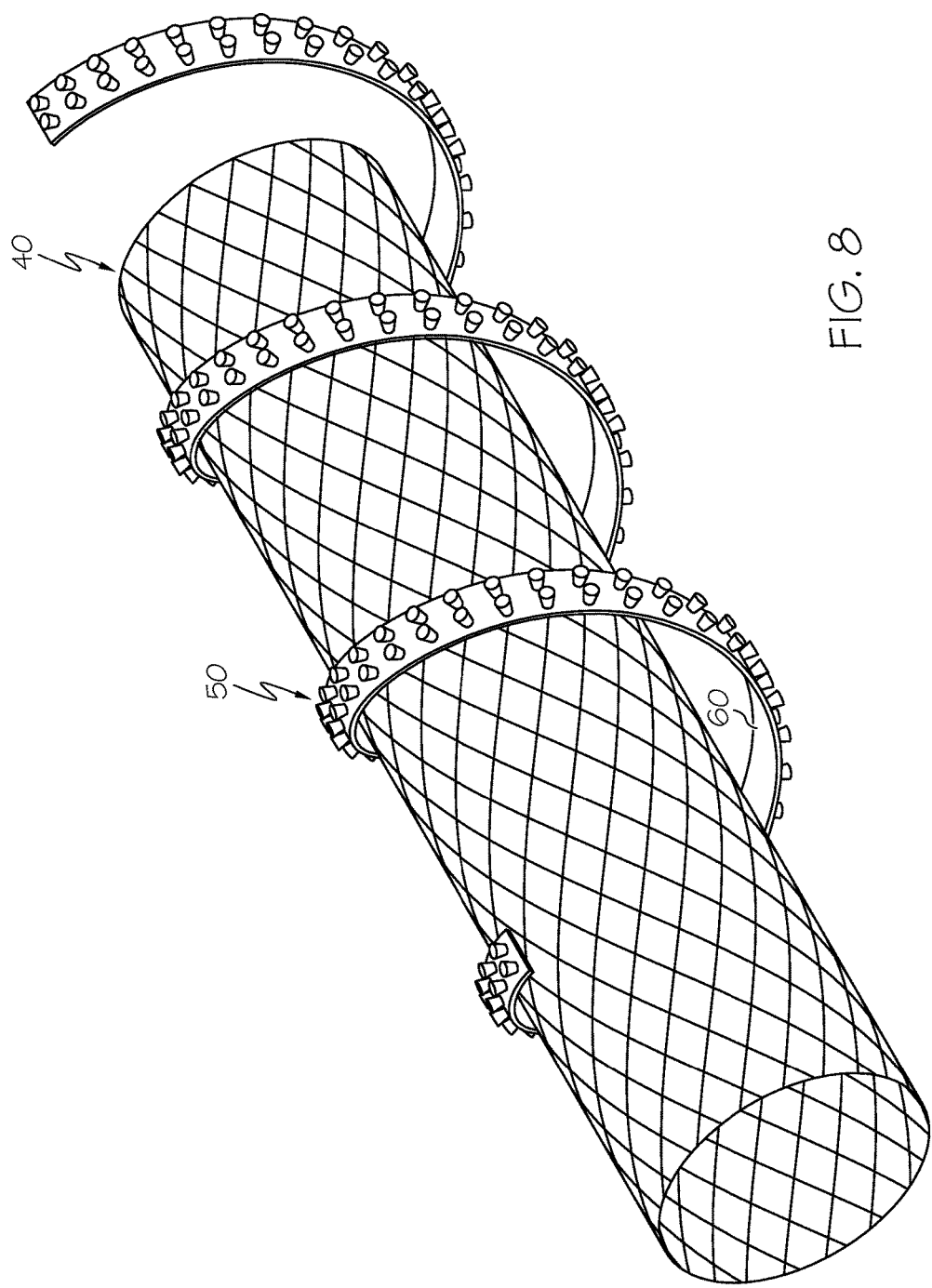

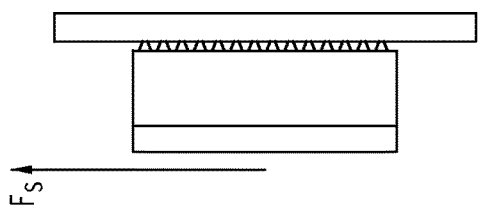
FIG. 9B
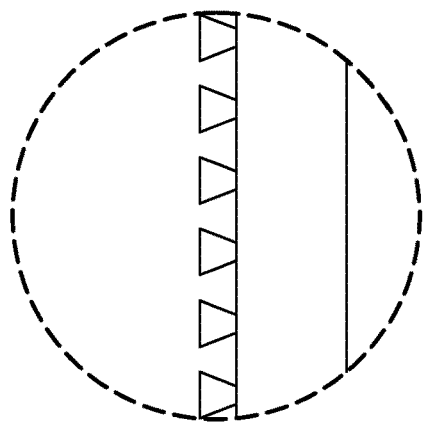
FIG. 9A(2)
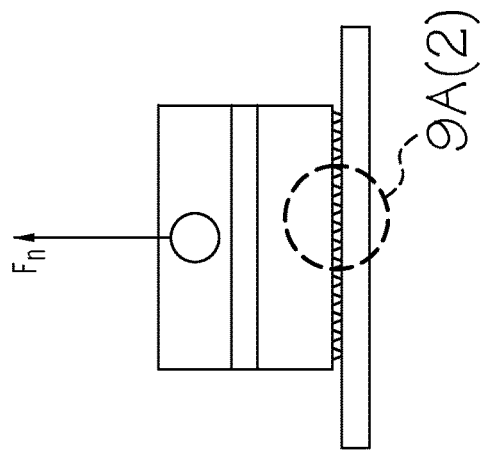
FIG. 9A(1)

COVERED ENDOSCOPIC STENTS WITH ADHESION ELEMENTS

CROSS REFERENCE TO RELATED APPLICATIONS

This application claims priority to U.S. Provisional Application No. 61/974,069 filed Apr. 2, 2014, the content of which is incorporated by reference in its entirety.

BACKGROUND

A stent is a medical device introduced into a body lumen and is well known in the art. A stent may be delivered in an unexpanded state to a desired location in a bodily lumen and then self-expand or be expanded by an internal radial force. Stents, grafts, stent-grafts, vena cava filters, expandable frameworks, and similar implantable medical devices, collectively referred to hereinafter as stents, have included radially expanding or expandable endoprostheses, which have been used as intraluminal implants capable of being implanted transluminally.

Gastrointestinal stents have been used to treat patients suffering from a range of malignant and non-malignant diseases. For example, esophageal stents have been associated with the treatment of esophageal cancers. Esophageal stents have also been used to reduce symptoms resulting from non-esophageal tumors that grow to obstruct the esophagus and to treat benign esophageal disorders, including but not limited to refractory strictures, fistulas and perforations. In each of these cases, esophageal stents may provide mechanical support to the esophageal wall and may maintain luminal patency. Because of the structure of the esophagus and conditions such as peristalsis, esophageal stents have been prone to stent migration.

One way to reduce the risk of stent migration has been to expose bare metal portions of the stent to tissue. The open, braided structure of the stent may provide a scaffold that promotes tissue ingrowth into the stent. This tissue ingrowth may aid anchoring the stent in place and may reduce the risk of migration. In some cases, however, tissue ingrowth has been known to lead to reocclusion of the lumen. In addition, stents anchored by tissue ingrowth cannot be moved or removed without an invasive procedure. To reduce tissue ingrowth, stents have been covered with a coating (e.g., made of a polymer, etc.) to create a physical barrier between the lumen and the tissue wall. However, in some circumstance, such stents can have an unacceptable occurrence of migration, as compared to bare metal counterparts.

Another way to reduce the risk of stent migration has been to use a flared stent. However, stents having flares can have an unacceptable occurrence of migration.

Improved stents with, for example, improved resistance to migration, improved stent adhesion, and/or improved removability are desired. Previous stents, such as those discussed in US Patent Publication Nos. 2006/0069425 and 2009/0062927, which are incorporated by reference herein in their entireties, have incorporated bumps or other surface features incorporated into the stent itself. Another stent described in co-owned US Patent Publication No. 2012/0035715, which is incorporated by reference herein in its entirety, provides a plurality of surface protrusions on the outer surface of the stent.

Without limiting the scope of the present disclosure, a brief summary of some of the claimed embodiments is set forth below. Additional details of the summarized embodiments of the present disclosure and/or additional embodiments of the present disclosure may be found in the Detailed Description below. A brief abstract of the technical disclosure in the specification is also provided. The abstract is not intended to be used for interpreting the scope of the claims.

BRIEF SUMMARY

The present disclosure provides an endoprosthesis where a preferably polymeric cover has a number of adhesion elements arranged in a micropattern. As used herein, a micropattern may include a regular or irregular array of adhesion elements.

In at least one embodiment, an endoprosthesis, having an expanded state and a contracted state, includes a stent with a polymeric cover on an outer surface of the stent. The stent has an inner surface defining a lumen. In at least one embodiment, the stent is a flared stent. The polymeric cover includes a base and adhesion elements. In some embodiments, the adhesion elements extend outwardly from the outer surface of the base (outwardly extending adhesion elements). In other embodiments, the adhesion elements extend inwardly from the outer surface of the base (inwardly extending adhesion elements). In at least one embodiment, the adhesion elements are arranged in a micropattern. When the endoprosthesis expands to the expanded state in a lumen defined by a vessel wall, the adhesion elements create an interlock between the vessel wall and the endoprosthesis.

The micropattern can be a grid pattern, a rectangular array, a regular n-polygonal array, helical, and combinations thereof. The micropattern can be specifically designed for a particular implantation site. For example, the width d, number, and spacing s of the adhesion elements can be selected to achieve a desired level of device fixation. In at least one embodiment, the micropattern is present along at least a portion of the endoprosthesis. In at least one embodiment, the adhesion elements of the micropattern can be uniform, or the micropattern can be formed of outwardly extending adhesion elements and inwardly extending adhesion elements.

In at least one embodiment, the endoprosthesis is retrievable by, for example, a retrieval loop at a distal end of the endoprosthesis. In some embodiments, the endoprosthesis is retrievable by a retrieval loop at a proximal end and a retrieval loop at a distal end of the endoprosthesis.

Several methods of manufacturing an embodiment of the endoprosthesis are provided. One method of manufacturing includes forming a polymeric cover, wherein the polymeric cover includes a base and adhesion elements; providing a stent having an inner surface defining a lumen and an outer surface; and adhering, securing, or connecting the base of the polymeric cover to the outer surface of the stent. In at least one embodiment, the adhesion elements are arranged in a micropattern. The adhesion elements can be inwardly extending adhesion elements; outwardly extending adhesion elements; and combinations thereof. A polymeric cover with adhesion elements can be formed using a mold having an inverse of the micropattern and injecting a polymeric material into the mold and, in some cases, applying temperature or pressure to the mold before the polymeric material cures; using soft lithography techniques; or by etching the polymeric cover from a layer of the polymeric material. In at least one embodiment, an adhesive layer is applied to at least one of a surface of the base and the outer surface of the stent. In at least one embodiment, the polymeric cover is formed as a tubular structure. In one or more embodiments, the polymeric cover is formed in a strip, which wraps (e.g., helically wrapped, circumferentially wrapped, randomly wrapped, etc.) around the outer surface of the stent.

BRIEF DESCRIPTION OF THE SEVERAL VIEWS OF THE DRAWING(S)

FIG. 1 shows a plan view of an endoprosthesis embodiment of the present disclosure.

FIG. 2 shows a cross-section of the endoprosthesis shown in FIG. 1.

FIG. 6A-E show exemplary micropatterns.

Figure 7:
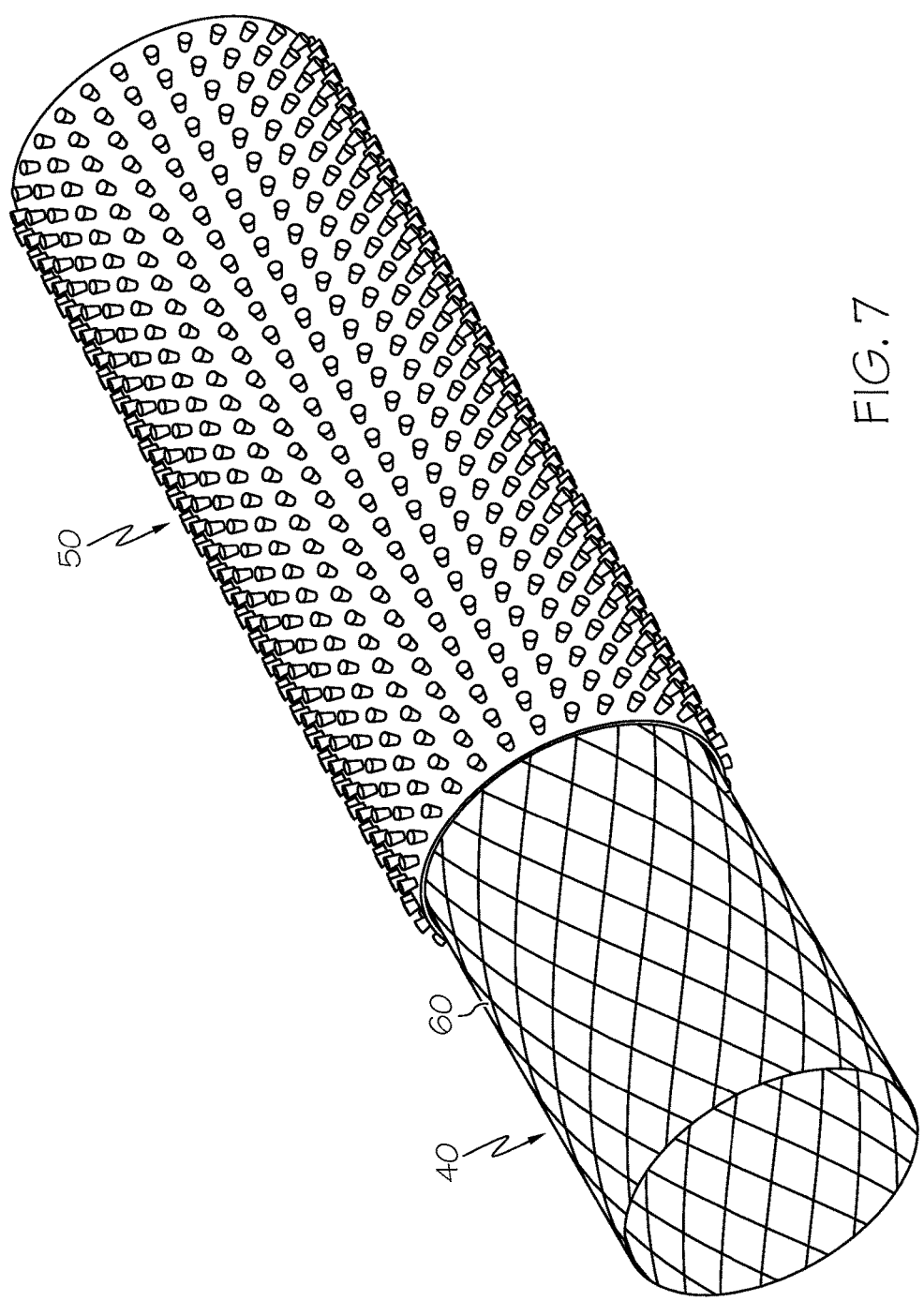

FIG. 7 is a view of a stent and polymeric cover during one method of manufacturing an endoprosthesis.

FIG. 8 is a view of a stent and polymeric cover during one method of manufacturing an endoprosthesis.

FIGS. 9A(1) and 9A(2) shows the normal force of a stent with an embodiment of a covering with adhesion elements.

FIG. 9B shows the shear force of a stent with an embodiment of a covering with adhesion elements.

DETAILED DESCRIPTION

While the subject matter of the present disclosure may be embodied in many different forms, there are described in detail herein specific preferred embodiments of the present disclosure. This description is an exemplification of the principles of the present disclosure and is not intended to limit the present disclosure to the particular embodiments illustrated.

For the purposes of this disclosure, like reference numerals in the figures shall refer to like features unless otherwise indicated.

The present disclosure relates to micropatterned polymeric covers for use on medical devices. In some embodiments, the micropatterned polymeric covers are utilized with implantable medical devices, such as stents, to reduce or prevent stent migration, particularly for stents used in the gastrointestinal or pulmonary systems, including, but not limited to, tracheal, esophageal, biliary, and colonic stents. The endoprostheses described in this application may be also used in the cardiovascular system, and elsewhere in the body (e.g., any body lumen).

FIGS. 1 and 2 show an endoprosthesis 20 with a proximal end 22 and a distal end 24. The endoprosthesis 20 includes an expandable stent 40 and a polymeric cover 50 on the outer surface of the expandable stent 40. Expandable stent 40 can be self-expanding, balloon expandable, or hybrid expandable. Embodiments of the expandable stent 40 contemplate stents having a constant diameter, tapers, flares and/or other changes in diameter in the body and/or at an end or ends. The expandable stent 40 has an inner surface 42, an outer surface 44, a proximal end 46, and a distal end 48. The polymeric cover 50 is positioned about at least a portion of the outer surface 44.

In at least one embodiment, the polymeric cover 50 substantially covers the entire outer surface 44 of the expandable stent 40. In other embodiments, the polymeric cover 50 covers a portion of the outer surface 44 of the expandable stent 40. As shown in FIG. 2, the polymeric cover 50 can be directly connected to the outer surface 44 of the expandable stent 40. In one or more embodiments, the polymeric cover 50 can be connected to the outer surface 44 of the expandable stent 40 using an adhesive or other means of attaching the cover to the device. In at least one embodiment, the polymeric cover at least partially covers the inner surface 42 as well. In at least one embodiment, partial coverage can include partial coverage of the perimeter and/or the length.

In at least one embodiment, the polymeric cover 50 includes a base 52 and a plurality of adhesion elements 54. In at least one embodiment, the adhesion elements are seamlessly incorporated into the base of the cover. In at least one embodiment, the base 52 is coterminous with the expandable stent 40. What is meant by "coterminous" is that the base 52 of the polymeric cover 50 and the expandable stent 40 have the same boundaries, cover the same area, and are the same in extent. In other words, the expandable stent 40 and the base 52 each have first and second ends, the expandable stent 40 and the base 52 extend between their first and second ends, the first end of the expandable stent 40 is the same as first end of the base 52, and the second end of the expandable stent 40 is the same as the second end of the base 52. Since the expandable stent 40 and the base 52 extend between their first and second ends, the expandable stent 40 and the base 52 have the same boundaries, cover the same area, and are the same in extent. Thus, the base 52 and the expandable stent 40 are coterminous. The expandable stent 40 and the base 52 therefore are coterminous in at least one embodiment. Also, base 52 is tubular in at least one embodiment.

As discussed above, in at least one embodiment, the polymeric cover at least partially covers the inner surface 42 as well. For these embodiments, the adhesion elements 54 only form a part of the polymeric cover 50 that at least partially covers the outer surface of the stent and do not form a part of the polymer cover that covers the inner surface of the stent. In some embodiments, the endoprosthesis as disclosed herein can be described as having an outer surface comprising a plurality of adhesion elements and an inner surface free of adhesion elements.

"Adhesion elements" as used herein are structures that create a partial vacuum in order to adhere, stabilize, fix, or immobilize the implanted endoprosthesis to the lumen wall. A "partial vacuum" as used herein refers to a negative gauge pressure inside the adhesion element with respect to the pressure outside the adhesion element. The partial vacuum between the adhesion element and the lumen wall is similar to the partial vacuum created by a suction cup.

Without being bound by theory, expansion of the endoprosthesis upon deployment in a body lumen provides a radial force that engages the adhesion elements to the lumen wall and a partial vacuum is created due to a decrease in the area between the adhesion element and the lumen wall. Continued engagement with the lumen wall is the result of a radial force generated by the stent against the lumen wall. For an implanted endoprosthesis, if the adhesion elements become disengaged from the wall, periodic radial peristaltic forces can reengage the adhesion elements to the wall. Further, any liquid that accumulates between the adhesion element and the wall can be periodically removed due to the peristaltic forces.

As discussed below in greater detail, the cover 50 can include adhesion elements 54 that extend outwardly from the base 52 (outwardly extending adhesion elements), as shown for example in FIGS. 1-3; adhesion elements 54 that extend inwardly from the base 52 (inwardly extending adhesion elements), as shown for example in FIG. 4; and a combination of outwardly extending adhesion elements and inwardly extending adhesion elements (not shown).

Outwardly Extending Adhesion Elements

As discussed above, in some embodiments the adhesion elements 54 are outwardly extending adhesion elements 54a. Each outwardly extending adhesion 54a element extends radially outward from the outer surface of the base. In at least one embodiment, the outwardly extending adhesion elements extend at an angle, e.g. perpendicularly, from the outer surface of the base 52 (e.g., FIG. 3).

Figure 5B:
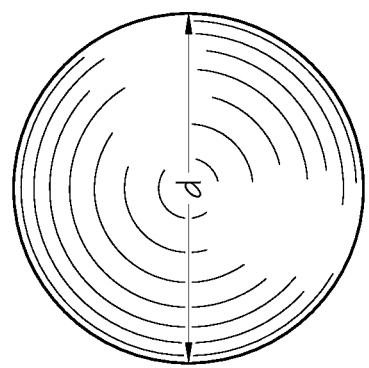
FIG. 5B is a top view of the adhesion element of FIG. 5A.
Figure 5A:
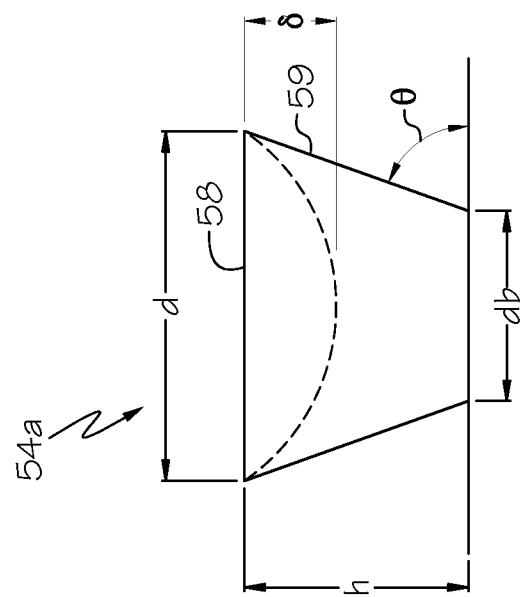
FIG. 5A is a side view of an adhesion element.

As shown for example in FIGS. 5A and 5B, each outwardly extending adhesion element 54a is a truncated cone with a concave end 58. It is noted that for simplicity some of the drawings do not show the concavity at the end of the truncated cone, however, each truncated cone of this embodiment has a concave end 58. Without being bound by theory, an adhesion element that is a truncated cone and has a concave end can create a partial vacuum with a lumen wall.

Each outwardly extending adhesion element 54a has a height h that is the greatest distance between the outer surface of the base 52 and the end 58 of the adhesion element, and a width d that is the greatest distance between two opposite points of the adhesion element, such as opposing points of the side 59 of the adhesion element. For a circular shaped outwardly extending adhesion element, for example a truncated cone, the width d is the diameter. For the outwardly extending adhesion element 54a shown in FIG. 5A, the greatest distance between two opposite points is the diameter at the end 58 (hereinafter end diameter), with the diameter of the adhesion element tapering from the end diameter to a base diameter db that is measured at the outer surface of the base 52 of the polymeric covering 50. Thus, the base diameter db is less than end diameter, and the width d of the outwardly extending adhesion element is equal to the end diameter. In some embodiments, the diameter of the outwardly extending adhesion element continuously decreases from the end 58 to the outer surface of the base 52 of the polymeric covering 50.

In at least one embodiment, the width d of the outwardly extending adhesion element 54a is 50 μm to 500 μm. Suitable widths d include 50 μm, 91.5 μm, 100 μm, 150 μm, 200 μm, 250 μm, 300 μm, 350 μm, 400 μm, 450 μm, and 500 μm. Without being bound by theory, it is expected that outwardly extending adhesion elements with smaller widths d provide better adhesion performance.

In at least one embodiment, the width d of the outwardly extending adhesion element is greater than the height h of the outwardly extending adhesion element. In some embodiments, the outwardly extending adhesion element 54a has a height h that is 20-50% of the width d. For outwardly extending adhesion elements 54a with a width d in the range of 50 μm to 500 μm, the outwardly extending adhesion elements 54a have a height h in the range of 10 μm to 250 μm. A non-limiting example of a suitable height h is 34.2 μm. It is noted that the height h of the outwardly extending adhesion elements 54a affects the overall profile of the endoprosthesis, which in turn affects deliverability with a smaller overall profile having an enhanced deliverability than a larger overall profile. Also, without being bound by theory, the height h of the outwardly extending adhesion element can affect the adhesion of the outwardly extending adhesion element.

The concavity at the end 58 of the outwardly extending adhesion element 54a has depth δ that is the greatest distance between the end 58 and the bottom of the concave surface. This is shown for example in FIG. 5A. The concave surface depth δ can range from 10% to 20% of the width d of the outwardly extending adhesion element 54a. For outwardly extending adhesion elements 54a with a width d in the range of 50 μm to 500 μm, the outwardly extending adhesion elements have a concave surface depth δ of 5 μm to 100 μm. The concave surface depth δ is also less than the height h of the outwardly extending adhesion element 54a. Without being bound by theory, the concave surface depth is affected by the other dimensions of the outwardly extending adhesion element and the elasticity (durometer) of the material used to form the outwardly extending adhesion element.

As shown in FIG. 5A, the side 59 of the truncated cone extends at an angle θ from the outer surface of the base 52. In at least one embodiment the angle θ is an oblique angle relative to the outer surface of the base 52. As used herein an "oblique angle" is a non-parallel and a non-perpendicular angle. In at least one embodiment, the outwardly extending adhesion element 54a has a minimum angle θ of 30 degrees and a maximum angle θ of 75 degrees relative to the outer surface of the base of the polymeric cover. Thus, the range for the angle θ is 30-75 degrees.

In at least one embodiment, the outwardly extending adhesion elements are truncated cones with a width d selected from the range of 50 μm to 500 μm; a height h that is 20-50% of the width d; a concave surface depth δ that is 10-20% of the width d; and an angle θ selected from the range of 30 degrees to 75 degrees.

In one embodiment, the outwardly extending adhesion elements are truncated cones with a width d of 91.5 μm, a height h of 34.2 μm, a concave surface depth δ of 12.4 μm, and an angle θ of 63.9° relative to the outer surface of the base of the polymeric cover.

Inwardly Extending Adhesion Elements

As discussed above, in some embodiments, the adhesion elements are inwardly extending. This is shown for example in FIG. 4 which shows examples of two types of inwardly extending adhesion elements: an example of a crater 54b and examples of pores 54c. In one embodiment, the inwardly extending adhesion element have a circular shape. The inwardly extending adhesion elements 54b, 54c have a width d that is the greatest distance between two opposite points of the inwardly extending adhesion element, such as opposing points of the side 59 of the inwardly extending adhesion element. For a circular shaped inwardly extending adhesion element, e.g. as shown in FIG. 4, the width d is the diameter. A range of suitable widths d for the inwardly extending adhesion elements 54b, 54c is 10 μm to 100 μm. A suitable range of depths for the inwardly extending adhesion elements is 20-50% of the width d of the inwardly extending adhesion element. For an inwardly extending adhesion element with a width d of 10 μm to 100 μm, the depth δ would be 2 μm to 50 μm.

In some embodiments, the inwardly extending adhesion elements 54b, 54c have a diameter at the outer surface of the base that is greater than a diameter at the inner surface of the base, with the inwardly extending adhesion element having a width d equal to the diameter at the outer surface of the base. In other embodiments, the inwardly extending adhesion elements 54b, 54c have a diameter at the outer surface of the base that is smaller than a diameter at the inner surface of the base, with the inwardly extending adhesion element having a width d equal to the diameter at the inner surface of the base.

In one embodiment, the inwardly extending adhesion elements are craters 54b with a depth δ less than the thickness of the base 52. An example of a crater 54b is shown in FIG. 4. Each crater 54b has a wall 59 that defines a concavity having a depth δ that is less than the thickness t of the base 52 of the polymeric cover 50. As discussed above, the depth δ is 10-20% of the width d of the crater, and for a crater with a width d of 10 μm to 100 μm, the depth δ would be 2 μm to 50 μm, and the thickness t of the base 52 is greater than the depth δ. Each crater has a variable diameter from the outer surface of the base to the bottom of the concavity.

Figure 4:
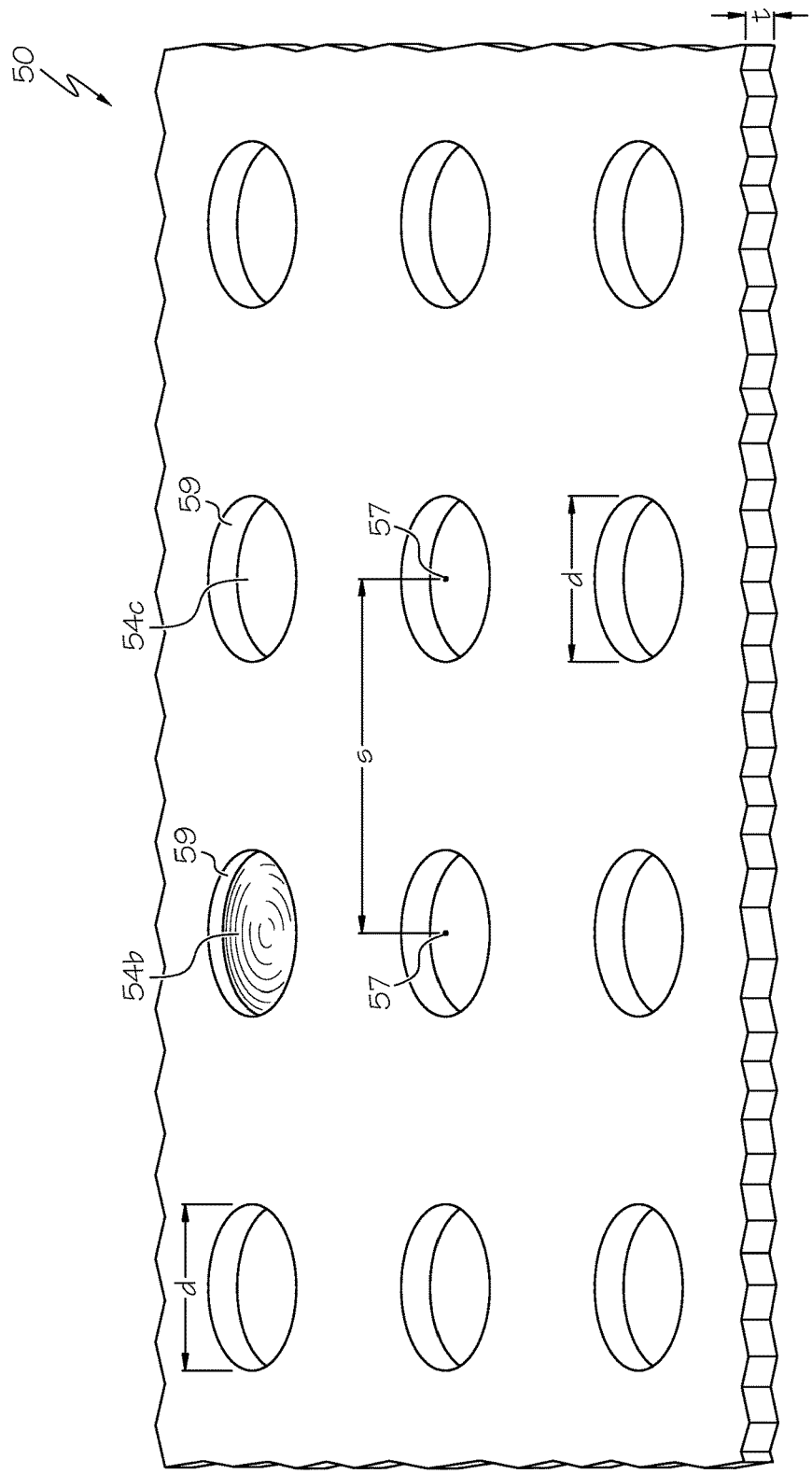
FIG. 4 is an enlarged view of a polymeric cover with inwardly extending adhesion elements.

In another embodiment, the inwardly extending adhesion elements are pores 54c with a depth equal to the thickness t of the base 52, as shown for example in FIG. 4. In other words, the pores 54c extend from an opening in the outer surface of the base to an opening in the inner surface of the base. In at least one embodiment the wall 59 of the pore 54c extends toward the center 57 of the pore 54c at an oblique angle to the base 52 to form the open concavity of the pore 54c.

In at least one embodiment, a period of time after implantation there is tissue ingrowth into the inwardly extending adhesion elements 54b, 54c. For craters 54b, tissue ingrowth does not extend into the lumen of the endoprosthesis, whereas for pores 54c tissue ingrowth extends into the lumen of the endoprosthesis.

Without being bound by theory, the partial vacuum between the lumen wall and the inwardly extending adhesion elements 54b, 54c help to stabilize the endoprosthesis in the short term while tissue ingrowth helps to provide long term fixation of the endoprosthesis. If tissue ingrowth occurs, the mechanism of fixation changes from the partial vacuum to tissue ingrowth. Depending on the amount of tissue ingrowth, there may or may not be a partial vacuum between the lumen wall and the inwardly extending adhesion element.

Adhesion Elements Arranged in Micropatterns

In at least one embodiment, the plurality of adhesion elements 54 can be arranged in one or more micropatterns 70 as shown for example in FIGS. 1 and 6A-8. In some embodiments, the micropattern(s) of a cover is formed only by outwardly extending adhesion elements 54a. In one embodiment, the outwardly extending adhesion elements have a uniform size. In other embodiments, the micropattern(s) of a cover is formed only by inwardly extending adhesion elements 54b, 54c. In one embodiment, the inwardly extending adhesion elements have a uniform size. In still further embodiments, the micropattern(s) of a cover is formed by outwardly extending adhesion elements 54a and by inwardly extending adhesion elements 54b, 54c. In one embodiment, the outwardly extending adhesion elements have a uniform size and the inwardly extending adhesion elements have a uniform size. For example, one area of the cover has outwardly extending adhesion elements arranged in a first micropattern and another area of the cover has inwardly extending adhesion elements arranged in a second micropattern (not shown).

Although not wishing to be bound by theory, the micropattern may affect the strength of the engagement or interlock between the endoprosthesis and the vessel wall. Likewise, the micropattern is dependent upon the desired engagement or interlock between the adhesion elements and the tissue. For this reason, in at least one embodiment, a particular microstructure can be selected that has a micropattern geometry and dimensions suitable for a particular application (e.g., implantation site, biological tissue, desired tissue engagement properties, etc.). Factors to consider are discussed below in greater detail.

In some embodiments, the polymeric cover has only one micropattern. In other embodiments, the polymeric cover has multiple micropatterns. Thus, the polymeric cover can be tailored to specific structural characteristics of the body lumen (e.g., a vessel, etc.) and a desired engagement or interlock can be achieved, while using a single endoprosthesis.

Figure 3:
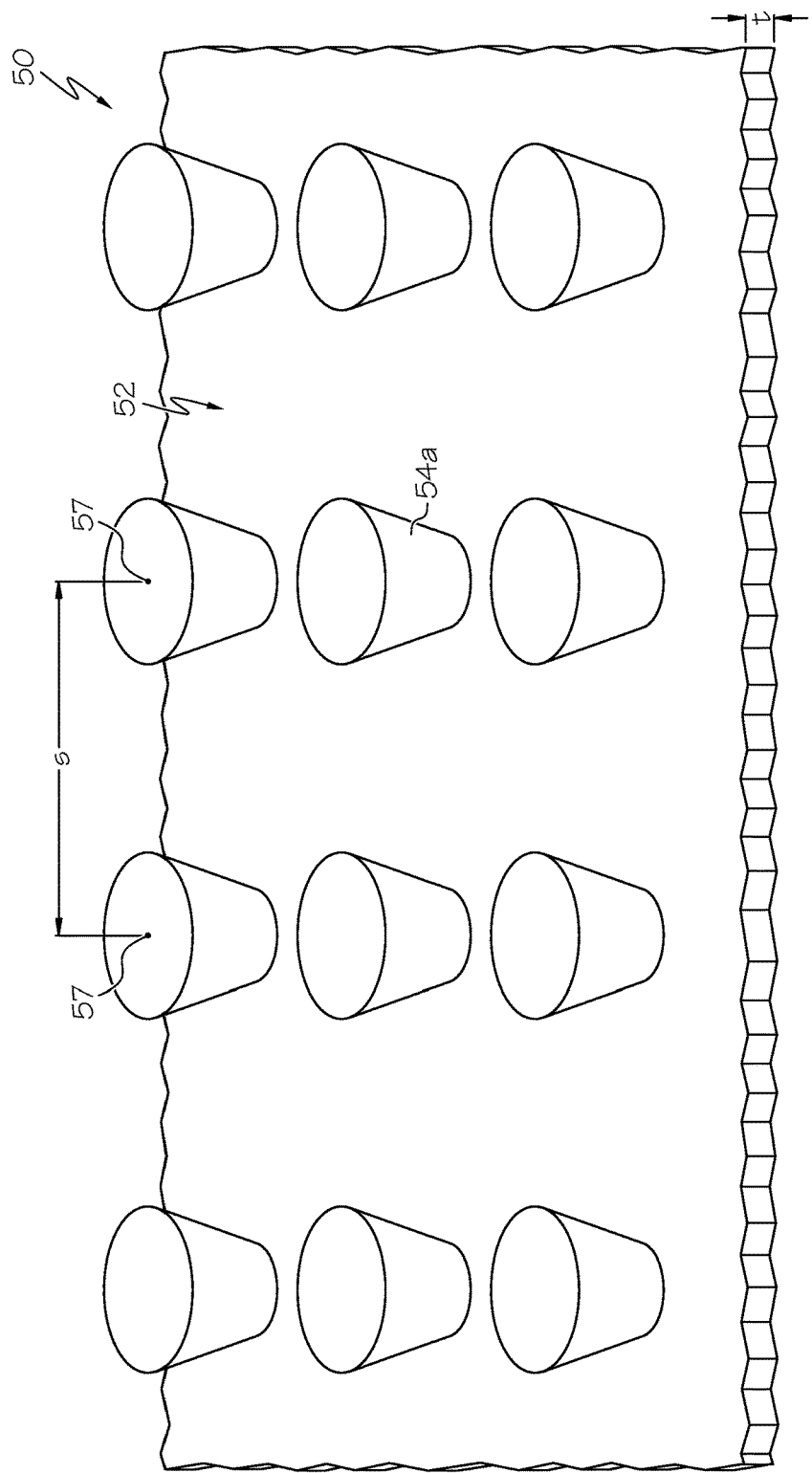
FIG. 3 is an enlarged view of a polymeric cover with outwardly extending adhesion elements.

In at least one embodiment, two adjacent adhesion elements 54 in a micropattern are spaced apart by a distance s measured between the centers 57 of two adjacent adhesion elements (shown in FIGS. 3 and 4). Thus, the spacing s is related to the density of the adhesion elements. Without being bound by theory, for a given width d, the closer the spacing s between adjacent adhesion elements in a micropattern, the greater the peel off force in the normal direction. For a given width d, the closer the spacing s between adjacent adhesion elements, the greater the peel off force in the shear direction. Also without being bound by theory, for a given width d and spacing s of adhesion elements in a micropattern, the peel off force in the normal direction is greater than the peel-off force in the shear direction. In at least one embodiment, the spacing s is 120 μm, 130 μm, 140 μm, or 150 μm. As discussed below in greater detail, the spacing s can be less than, equal to, or greater than the width d of the adhesion element, depending on the amount of adhesion desired. In at least one embodiment, the ratio of the spacing s to the width d is about 1.2.

Figure 6A:
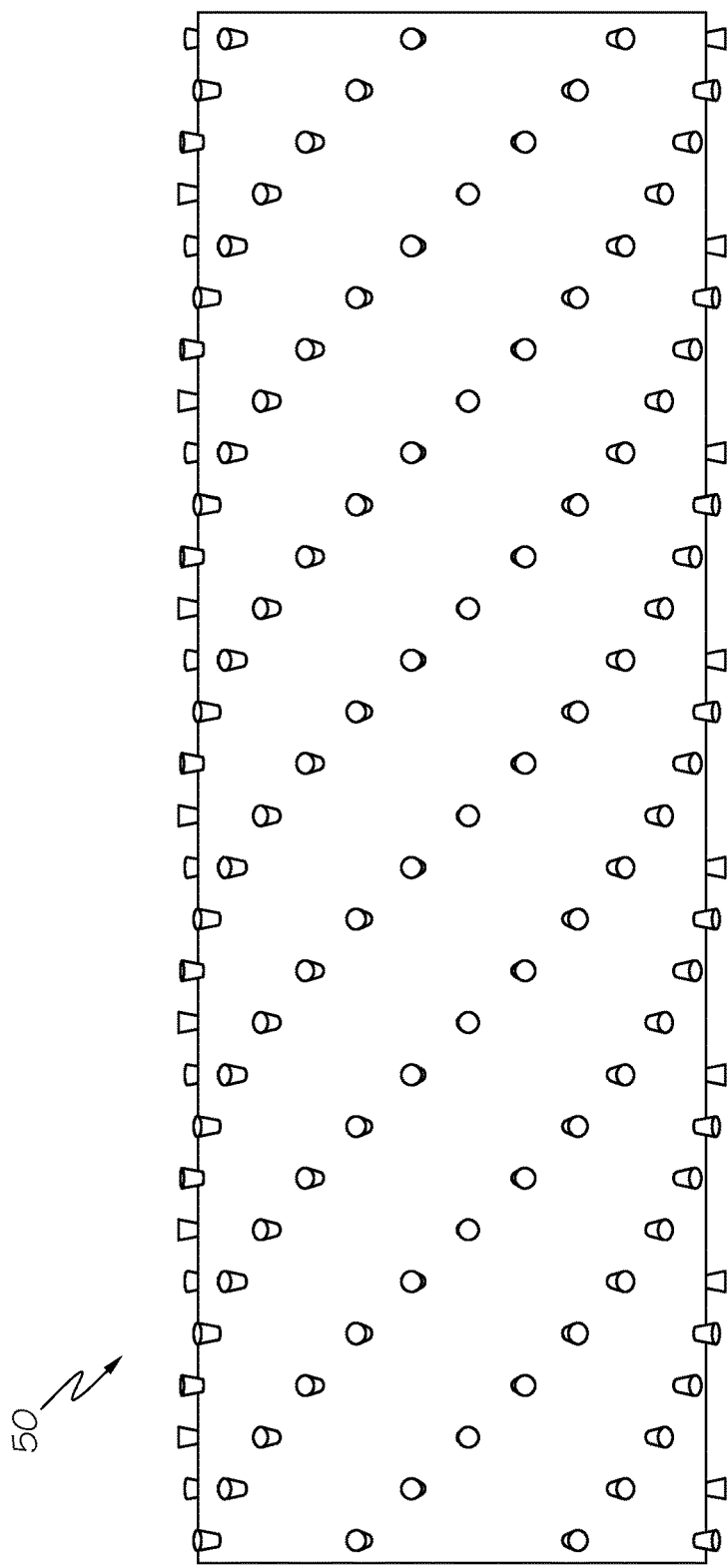
Figure 6B:
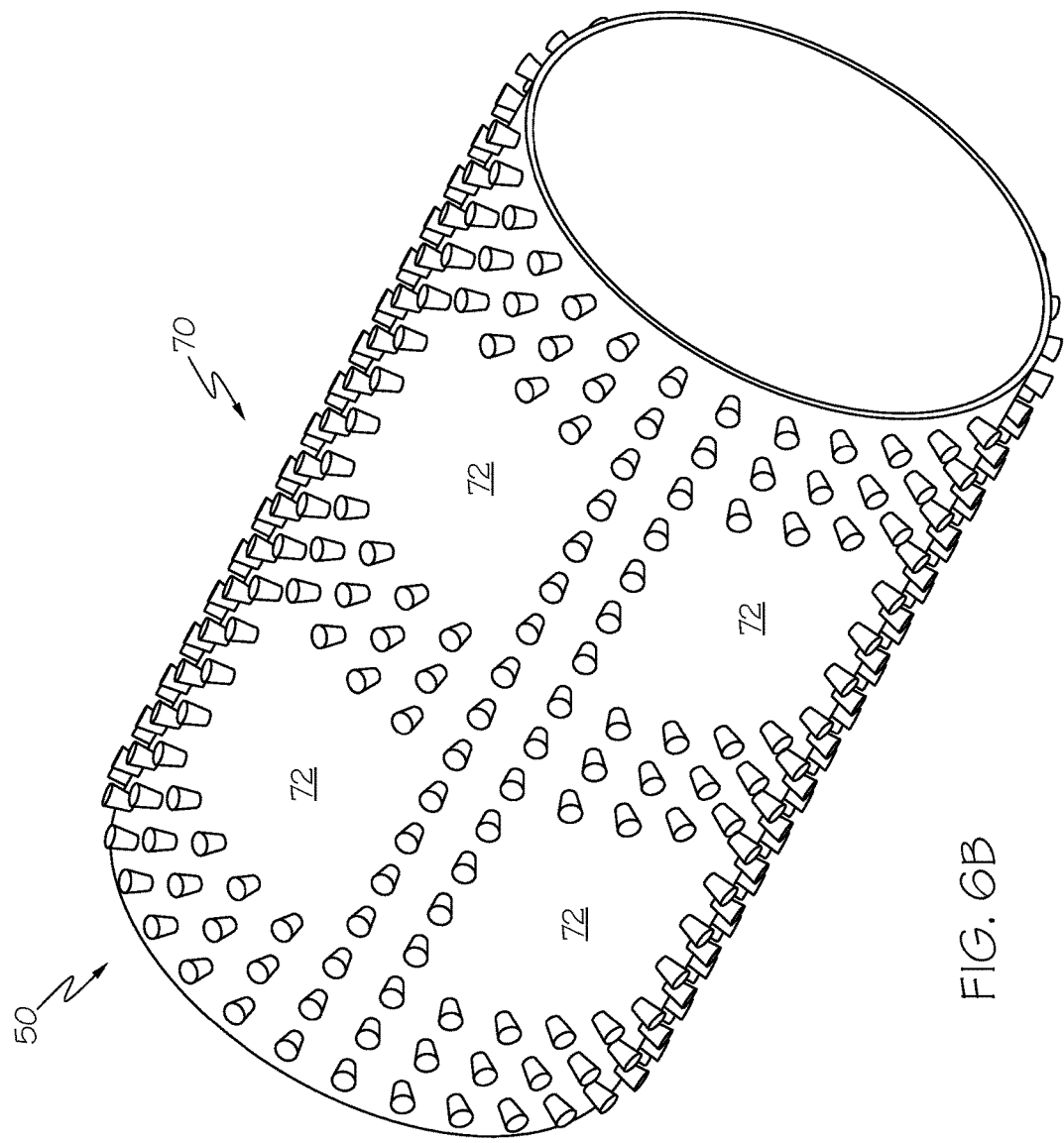

In at least one embodiment, the adhesion elements are spaced apart equidistantly in the micropattern. In this embodiment, the spacing s of the adhesion elements is uniform. In at least one embodiment, the micropattern 70 of adhesion elements is a rectangular array (e.g., FIG. 3, FIG. 6C). In at least one embodiment, the micropattern 70 is a grid pattern (e.g., a square array as in FIGS. 6C, 7). In at least one embodiment, the micropattern 70 is a regular n-polygonal array (e.g., hexagonal array in FIGS. 6D, 6E), wherein an adhesion element may be present in the center of the polygon (e.g., FIG. 6C, FIG. 6D, etc.) or may not be present in the center of the polygon (e.g., FIG. 6E). In other words, the adhesion elements are arranged in rows and columns in the micropattern, wherein the rows and columns may or may not be perpendicular. For example, the micropattern 70 of FIG. 6C includes rows and columns that are perpendicular, whereas the micropattern 70 of FIGS. 6D and 6E includes rows and columns that are not perpendicular. In one or more embodiments, each adhesion element has a longitudinal axis and the adhesion elements are axially aligned in at least one of the axial direction (e.g., arranged in a row parallel to a longitudinal axis of a stent) and the circumferential direction of the endoprosthesis (e.g., arranged in a row extending circumferentially around a longitudinal axis of a stent). In at least one embodiment, the micropattern of adhesion elements includes any or all of the features described in this paragraph. In some embodiments, like the embodiments shown in FIGS. 6A and 6B, the micropattern 70 may cover only a portion of the base 52 rather than the entire base 52. In other words one or more portions 72 of the base are free of adhesion elements. The micropattern 70 of adhesion elements may be helically disposed on the base 52, as shown in FIG. 6A. In one or more embodiments, as shown in FIG. 6B, a first micropattern 70 may be disposed longitudinally along the base 52 and a second micropattern 70 is disposed circumferentially about the base so that the micropattern forms a "window pane"-like configuration with portions 72 having no adhesion elements. As depicted in FIG. 6B, the adhesion elements arranged in a row (e.g., parallel to a longitudinal axis of a stent) may be continuous rows or discontinuous rows (e.g., aligned row segments separated by a gap having a dimension greater than the spacing s), wherein the length of the discontinuity may have any length (e.g., 2 or more times the dimension s). For example, the embodiment depicted in FIG. 6B shows discontinuous rows (and circumferentially oriented columns) extending across the window panes wherein the length of the discontinuity is five times the spacing s, whereas the embodiment depicted in FIG. 6E shows discontinuous rows (and nonperpendicularly oriented columns) wherein the length of the discontinuity is two times the spacing s. Thus, in FIGS. 6B and 6E, the spacing s of the adhesion elements is not uniform. In terms of the spacing s, a row and/or column discontinuity may have any length (e.g., at least 2 times s, at least 5 times s, at least 10 times s, at least 50 times s, at least 100 times s, at least 500 times s, at least 1000 times s, etc.).

In some embodiments, the spacing s between adjacent outwardly extending adhesion elements 54a is large enough so that the tissue of the bodily vessel can fill the negative space (e.g., void space) between the outwardly extending adhesion elements. In these embodiments, the endoprosthesis is secured to the vessel wall by two mechanisms: by the partial vacuum between the outwardly extending adhesion elements and the lumen wall, and by tissue ingrowth into the spaces between adjacent outwardly extending adhesion elements. If the spacing s is too small, the tissue may not be able to fill the space between the outwardly extending adhesion elements. If this is the case the endoprosthesis is secured to the vessel wall only by the partial vacuum between the outwardly extending adhesion elements and the lumen wall. In at least one embodiment, the spacing s between the adhesion element is dependent upon (e.g., may be selected based upon) the particular type of tissue of the bodily vessel.

In some embodiments, a spacing s for the outwardly extending adhesion elements in the range of 100-1000 μm provides for tissue ingrowth. In at least one embodiment, the adhesion elements have variable spacing s. For example, in some embodiments, there is a gradient of spacing s of 100 to 1000 μm for the adhesion elements along the longitudinal length and/or along the circumference of the endoprosthesis. Without being bound by theory, a spacing gradient stimulates tissue ingrowth.

Forces/Resisting Migration

An endoprosthesis implanted in the body lumen experiences forces which may cause migration of the endoprosthesis from an original implantation site. As discussed above, the adhesion elements (outwardly and inwardly extending) resist the forces due to a partial vacuum. FIGS. 9A(1) and 9A(2) show the normal force. A force in the normal direction for an individual adhesion element 54 is represented by the following equation:

$$(F_{AE})_{normal} = A_{AE} \cdot \Delta P$$

where $A_{AE}$ is the area of the concavity formed by the adhesion element (note that since $r = \frac{1}{2}d$, $\pi r^2 = \pi d^2/4$) and $\Delta P$ is the difference in pressure between the adhesion element and the exterior pressure.

A total force in the normal direction for a number of adhesion elements 54 is represented by the following equation:

$$(F_{tot})_{normal} = n \cdot A_{AE} \cdot \Delta P$$

FIG. 9B shows the shear force. As can be seen, the force in the shear direction is perpendicular to the force in the normal direction. A total force in the shear direction for a number of adhesion elements 54 is represented by the following equation:

$$(F_{tot})_{shear} \approx \frac{1}{2}(F_{tot})_{normal}$$

As discussed above, the stent can be implanted in the esophagus. The esophagus has a pressure characterized by the following equation:

$$P_{intra\text{-}esophageal} \approx P_{intra\text{-}thoracic} = P_{intra\text{-}pleural}$$

The following equation characterizes esophageal pressure during normal inspiration:

$$P_{intra\text{-}esophageal} - P_{atmospheric} \approx -8 \text{ mmHg}$$

The following equation characterizes esophageal pressure during forced inspiration:

$$P_{intra\text{-}esophageal} - P_{atmospheric} \approx -50 \text{ mmHg}$$

Since $P_{atmospheric} = 760$ mmHg $= 101{,}325$ Pa, $P_{intra\text{-}esophageal} \approx 10^5$ Pa.

$\Delta P \approx 10^5$ Pa, if the pressure inside the adhesion element (e.g. inside the concavity of the adhesion element) is considered to be negligible relative to the intra-esophageal pressure. The assumption of pressure inside the adhesion elements being negligible relative to the pressure in the vessel provides the upper bound for the force estimated to resist stent migration.

For example, based on the above, an endoprosthesis implanted in the esophagus and having a length of 100 mm, a diameter of 18 mm and an array of adhesion elements with a width d of 1.0 mm and a spacing s of 2.0 mm can be characterized by the following equations:

1. Number of adhesion elements along length of the endoprosthesis ($n_L$):

$$n_L = \frac{100 \text{ mm}}{2 \text{ mm}} = 50$$

2. Number of adhesion elements along circumference of the endoprosthesis ($n_C$):

$$n_C = \frac{\pi \cdot (18 \text{ mm})}{2 \text{ mm}} \approx 28$$

3. Total number of adhesion elements (n):

$$n = n_L \cdot n_C = (50) \cdot (28) = 1400$$

4. Total force in the normal direction:

$$(F_{tot})_{normal} = (1400) \cdot \left[\frac{\pi}{4} \cdot (10^{-3} \text{m})^2\right] \cdot (10^5 \text{ Pa}) \approx 110 \text{ N} = 11.2 \text{ kilogram} \cdot \text{force}$$

5. Total force in the shear direction (force to resist stent migration):

$$(F_{tot})_{shear} \approx \frac{1}{2}(F_{tot})_{normal} = 5.6 \text{ kilogram} \cdot \text{force}$$

These factors and equations can be used to tailor the endoprosthesis to specific structural characteristics of the body lumen (e.g., a vessel, etc.) and a desired amount of engagement or interlock. Further, as discussed above, tissue ingrowth can enhance the amount of engagement or interlock. Thus, the width d, number, and spacing s of the adhesion elements can be selected to achieve a desired level of device fixation at a desired implantation site.

Materials; Therapeutic Agents

Regarding material for the polymeric cover 50, it is important that the material be flexible enough for the adhesion elements to create a partial vacuum with the lumen wall and be able to withstand the processing for creating the polymeric cover 50. For example, the material needs to be flexible enough so that when the adhesion element presses against the lumen wall, the volume of space between the concavity of the adhesion element and the lumen wall is reduced to form a partial vacuum. Examples of acceptable materials include, but are not limited to, flexible silicones, polyurethane, styrene-block-isobutylene-block-styrene (SIBS), hydrogels, mucoadhesive substrate, pressure-sensitive adhesives, and other suitable elastomers, such as synthetic rubbers. Other acceptable materials include any flexible, biocompatible, and non-biodegradable polymer. In at least one embodiment, the polymeric cover 50 includes at least one therapeutic agent. In other embodiments, a coating may be applied to the polymeric cover 50 that includes a therapeutic agent. A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, paclitaxel, everolimus, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof.

In a preferred embodiment, the outwardly extending adhesion elements 54 and the base 52 are formed from the same material. In one or more embodiments, the outwardly extending adhesion elements 54 are formed from one material and the base 52 is formed from a different material. In one or more embodiments, the outwardly extending adhesion elements 54 are formed with layers of material, and these layers can be the same material or can be different materials depending on the characteristics required for the desired engagement of the endoprosthesis with the vessel wall. For inwardly extending adhesion elements, the base 52 forms the adhesion element and so the material of the base 52 is the material of the adhesion element.

Retrieval Element

Because the endoprosthesis 20 has improved engagement with the tissue wall when inserted into a lumen of the patient, removal of the endoprosthesis may be more difficult with some traditional removal techniques. In at least one embodiment, shown in FIG. 1, the endoprosthesis 20 is provided with a suture or removal loop 55 on one end of the stent. In at least one embodiment, the removal loop 55 is provided on a distal end of the stent. It should be noted the term "distal" as used herein refer to a direction away from a practitioner implanting the devices of the present disclosure, while the term "proximal" refers to a direction toward the practitioner implanting the devices of the present disclosure. While sutures or removal loops are well known in the art for removing endoprosthesis, typically sutures or removal loops are provided on the proximal end of the stent, in other words the closest end to the practitioner. In this embodiment, the suture or removal loop is applied to the opposite end of the endoprosthesis (the distal end of the stent). In at least one embodiment, the practitioner grabs the loop from inside the endoprosthesis, and by applying an axial force to the loop, the distal end of the endoprosthesis is pulled through the lumen of the endoprosthesis itself. Thus, the adhesion elements are peeled away from the vessel wall while the stent is flipped inside out to remove the endoprosthesis. In other embodiments, the practitioner may grab the loop from outside the endoprosthesis or at an end of the endoprosthesis.

In other embodiments, the endoprosthesis is provided with a suture or removal loop at both ends of the stent. In one embodiment, the distal loop is pushed distally as the proximal loop is pulled proximally thereby stretching the endoprosthesis axially and thus reducing the diameter of the endoprosthesis. The decrease in diameter can be induced in a progressive fashion from the ends to the center (mid-point along the length) of the endoprosthesis. Without being bound by theory, a progressive reduction in diameter causes the adhesion elements to disengage from the vessel lumen in a sequential fashion minimizing the retrieval force and thus any trauma to the vessel wall.

Manufacturing A Polymeric Cover with Adhesion Elements

To manufacture a cover 50 with adhesion elements 54, several methods can be employed. The polymeric cover 50 can be molded separately from the stent and then adhered to the stent with an adhesive layer 60 between the outer surface of the endoprosthesis and the base of the polymeric cover. Polymeric material can be injected into a mold with the inverse of the micropattern to create the polymeric cover. Also, the polymeric material can be pulled through a mold using a vacuum pump system. In at least one embodiment, the polymeric cover can be created using soft lithography techniques. In one or more embodiments, etching techniques can be used to create the cover, wherein material is taken away from a layer of the cover material to create the micropattern of the polymeric cover 50. In yet another embodiment, a technique called hot embossing can be used, which involves stamping partially cured polymer into the desired shape of the polymeric cover and then curing it before it is applied to the stent. Stamping may or may not include the use of a solvent.

In at least one embodiment, as shown in FIG. 7, the cover 50 can be molded as a substantially tubular structure with a lumen defined by the base of the cover. An adhesive layer 60 can be applied to either the stent or to at least a portion of the inner surface of the base of the cover. In at least one embodiment, the adhesive layer 60 may substantially cover the entire inner surface of the base of the cover. The stent 40 can be inserted into the lumen of the cover 50. In at least one embodiment, heat and/or pressure may be applied to ensure proper adhesion of the cover 50 to the stent 40 via the adhesive layer 60. The adhesive layer may include silicone coatings, other suitable adhesives, or priming solutions that enable the cover to adhere to the metal stent (or stent coating thereon).

In one or more embodiments, as shown in FIG. 8, rather than being molded as a tubular structure, the cover 50 can be molded as a strip attached to the outer surface 44 of the stent 40. In some embodiments, the strip can be applied as perimeter strips attached circumferentially about at least a portion of the circumferential perimeter of the stent. In some embodiments, the strip can be a longitudinal strip attached to the stent in a longitudinal direction. In some embodiments, the cover can be helically wrapped about the stent, as shown in FIG. 8. In some embodiments the cover may be applied as a single strip or as multiple strips. Where the cover is applied as multiple strips, directly adjacent strips may abut one another or may be spaced apart from one another. In at least one embodiment, the strips may be partial tubular structures that extend along the length of the stent but only cover a portion of the circumference of the stent. In some embodiments, a portion of stent 40 may be exposed. An adhesive layer 60 can be applied to either the stent or to at least a portion of the base of the cover. In at least one embodiment, heat and/or pressure may be applied to ensure proper adhesion of the cover 50 to the stent 40 via the adhesive layer 60. In at least one embodiment, discrete micropatterns of adhesion elements can be formed on and/or attached directly to either the stent 40 or the polymeric cover 50.

In one or more embodiments, the polymeric cover 50 can be formed by dip-coating the stent 40 in the cover material without needing an additional adhesive layer to connect the cover 50 to the stent 40. For instance, the stent 40 can be inserted into a mold, which includes a cavity and a tubular member. The cavity is defined by an inner wall of mold, which is an inverse of the desired micropattern. The stent 40 rests on the tubular member such that the inner surface of the stent is disposed about the tubular member. The mold with the stent 40 can be dipped into the cover material so that the cover material fills the mold and attaches to the stent 40. In some embodiments, temperature changes and/or pressure changes may be applied to the mold to cure the cover material. Once the cover material cures to form the polymeric cover 50, the endoprosthesis 20 can be removed from the mold. Alternatively, the polymeric cover 50 can be injection molded onto the stent using a similar mold. The cover material is injected into the mold rather than the mold being dipped into the cover material.

EXAMPLES

A description of some exemplary embodiments of the present disclosure is contained in the following numbered statements:

Statement 1. An endoprosthesis comprising:

a stent, wherein the stent has an inner surface defining a lumen, an outer surface, a first end, a second end, and a thickness defined between the inner surface and the outer surface, wherein the stent has a plurality of openings extending through the thickness; and a polymeric cover on the outer surface of the stent, the polymeric cover comprising a base and adhesion elements, wherein the adhesion elements are arranged in a micropattern, wherein the base covers at least some of the openings of the stent.

Statement 2. The endoprosthesis of statement 1, wherein the endoprosthesis is expandable from an unexpanded state to an expanded state.

Statement 3. The endoprosthesis of any one of statements 1-2, wherein when in a body lumen with a wall, the micropattern of adhesion elements apply a force that creates a desired interlock between the wall and the endoprosthesis.

Statement 4, The endoprosthesis of any one of statements 1-3, wherein the adhesion elements are outwardly extending adhesion elements.

Statement 5. The endoprosthesis of statement 4, wherein each outwardly extending adhesion element has a width and a height.

Statement 6. The endoprosthesis of any one of statements 1-5, the outwardly extending adhesion element being a truncated cone.

Statement 7. The endoprosthesis of any one of statements 5-6, wherein the width of the adhesion element is about 50 μm to about 500 μm.

Statement 8. The endoprosthesis of any one of statements 5-6, wherein the adhesion element has a maximum width of 500 μm.

Statement 9. The endoprosthesis of any one of statements 5-6, wherein the adhesion element has a minimum width of 50 μm.

Statement 10. The endoprosthesis of any one of statements 5-9, wherein the height of the adhesion element is 20-50% of the width.

Statement 11. The endoprosthesis of any one of statements 5-10, wherein the outwardly extending adhesion element has a concave end.

Statement 12. The endoprosthesis of statement 11, wherein the concave end has a concave surface depth.

Statement 13. The endoprosthesis of statement 12, wherein the concave surface depth is 10-20% of the width.

Statement 14. The endoprosthesis of any one of statements 5-13, the outwardly extending adhesion element has a side extending at an oblique angle from the base.

Statement 15. The endoprosthesis of statement 14, wherein the oblique angle is about 30 degrees to about 75 degrees.

Statement 16. The endoprosthesis of any one of statements 1-4, wherein the outwardly extending adhesion elements are truncated cones with a width selected from the range of 50 μm to 500 μm; a height that is 20-50% of the width; a concave surface depth that is 10-20% of the width; and an angle θ selected from the range of 30 degrees to 75 degrees.

Statement 17. The endoprosthesis of any one of statements 1-4, wherein the outwardly extending adhesion elements are truncated cones with a height of 34.2 μm, a width of 91.5 μm, a concave surface depth of 12.4 μm, and an angle of 63.9°.

Statement 18. The endoprosthesis of any of statements 1-3, wherein the adhesion elements are inwardly extending adhesion elements.

Statement 19. The endoprosthesis of statement 18, wherein the inwardly extending adhesion elements are selected from the group consisting of craters, pores and combinations thereof.

Statement 20. The endoprosthesis of statement 18, the inwardly extending adhesion elements having a depth at most equal to a thickness of the base of the polymeric cover.

Statement 21. The endoprosthesis of statement 20, the depth being less than the thickness of the base.

Statement 22. The endoprosthesis of statement 20, the depth being equal to the thickness of the base.

Statement 23. The endoprosthesis of any one of statements 19-22, the inwardly extending adhesion elements having a width of about 50 μm to 500 μm.

Statement 24. The endoprosthesis of any one of statements 1-23, wherein the polymeric cover is a polymeric material.

Statement 25. The endoprosthesis of statement 24, wherein the polymeric material is elastic.

Statement 26. The endoprosthesis of any one of statements 24-25, wherein the polymeric material comprises silicone.

Statement 27. The endoprosthesis of any one of statements 1-26, wherein the micropattern is selected from the group consisting of a grid pattern; a rectangular array; a regular n-polygonal array; helical; and combinations thereof.

Statement 28. The endoprosthesis of any one of statements 1-26, wherein the adhesion elements are aligned into rows and columns.

Statement 29. The endoprosthesis of statement 28, wherein the rows and columns are perpendicular to one another.

Statement 30. The endoprosthesis of statement 28, wherein the rows and columns are at an oblique angle relative to one another.

Statement 31. The endoprosthesis of any one of statements 1-30, wherein the adhesion element in the micropattern having a spacing selected from the group consisting of 120 μm, 130 μm, 140 μm, and 150 μm.

Statement 32. The endoprosthesis of any one of statements 1-31, wherein the spacing is uniform.

Statement 33. The endoprosthesis of any one of statements 1-31, wherein the spacing is not uniform.

Statement 34. The endoprosthesis of any one of statements 1-17 and 25-33, wherein all of the adhesion elements are outwardly extending adhesion elements.

Statement 35. The endoprosthesis of any one of statements 1-3 and 19-33, wherein all of the adhesion elements are inwardly extending adhesion elements.

Statement 36. The endoprosthesis of any one of statements 1-35, wherein the adhesion elements comprise outwardly extending adhesion elements and inwardly extending adhesion elements.

Statement 37. The endoprosthesis of any one of statements 1-36, further comprising a retrieval element at a distal end of the endoprosthesis.

Statement 38. The endoprosthesis of statement 37, further comprising a retrieval element at a proximal end of the endoprosthesis.

Statement 39. The endoprosthesis of any one of statements 1-38, wherein the polymeric cover is a helical strip on the outer surface of the stent.

Statement 40. The endoprosthesis of any one of statements 1-38, wherein the polymeric cover is tubular and has a longitudinal length equal to a longitudinal length of the stent.

Statement 41. A method of manufacturing an endoprosthesis comprising:
forming a polymeric cover, wherein the polymeric cover comprises a base and adhesion elements arranged in a micropattern;
providing a stent having an inner surface defining a lumen and an outer surface; and
adhering the base of the polymeric cover to the outer surface of the stent.

Statement 42. The method of statement 41, wherein the polymeric cover is formed using a mold having an inverse of the micropattern and injecting a polymeric material into the mold.

Statement 43. The method of statement 41, wherein the adhesion elements are selected from the group consisting of outwardly extending adhesion elements, inwardly extending adhesion elements, and combinations thereof.

Statement 44. The method of any one of statements 41-43, wherein an adhesive layer is applied to at least one of a surface of the base and the outer surface of the stent.

Statement 45. The method of any one of statements 41-44, wherein the polymeric cover is formed in a strip and helically wrapped around the outer surface of the stent.

Statement 46. The method of any one of statements 41-44, wherein the polymeric cover is tubular.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

Further, the particular features presented in the dependent claims can be combined with each other in other manners within the scope of the present disclosure such that the present disclosure should be recognized as also specifically directed to other embodiments having any other possible combination of the features of the dependent claims.

This completes the description of the preferred and alternate embodiments of the present disclosure. Those skilled in the art may recognize other equivalents to the specific embodiment described herein which equivalents are intended to be encompassed by the claims attached hereto.

The invention claimed is:
1. An endoprosthesis comprising:
a stent, wherein the stent has an inner surface defining a lumen, an outer surface, a first end, a second end, a thickness defined between the inner surface and the outer surface, and a plurality of openings extending through the thickness; and
a polymeric cover on the outer surface of the stent, the polymeric cover comprising a base and adhesion elements arranged in a micropattern, wherein the base covers at least some of the plurality of openings of the stent; wherein the adhesion elements are truncated cones with a circular outer wall, the adhesion elements extending radially outwardly from a first end of the adhesion elements at an outer surface of the base of the polymeric cover to a second end of the adhesion elements opposite the first end, the second end defining a concave surface, the adhesion elements having a first width at the first end and a second width at the second end, the second width being larger than the first width, wherein the circular outer wall extends outward from the first end to the second end at an oblique angle relative to the outer surface of the base;
wherein the combined truncated cone and concave end structure of the adhesion elements is configured to create a partial vacuum between the adhesion elements and a body lumen wall to adhere the endoprosthesis to the body lumen wall.

2. The endoprosthesis of claim 1, wherein when the endoprosthesis expands in a lumen defined by a vessel wall, the micropattern of adhesion elements applies a force that creates a desired interlock between the vessel wall and the endoprosthesis.

3. The endoprosthesis of claim 1, wherein the second width is 50 μm to 500 μm, a height measured from the first end to the second end is 20-50% of the second width, and the concave surface has a depth that is 10-20% of the second width, and the oblique angle being 30-75 degrees.

4. The endoprosthesis of claim 1, wherein the micropattern is selected from the group consisting of a grid pattern; a rectangular array; a regular n-polygonal array; helical; and combinations thereof.

5. The endoprosthesis of claim 1, wherein the polymeric cover comprises silicone.

6. The endoprosthesis of claim 1, wherein the adhesion elements are uniform.

7. The endoprosthesis of claim 1, wherein the polymeric cover is tubular with a longitudinal length equal to a longitudinal length of the stent.

8. The endoprosthesis of claim 1, further comprising a retrieval element at a distal end of the endoprosthesis.

9. The endoprosthesis of claim 1, wherein the adhesion elements have a height measured from the first end to the second end of the adhesion element, and the concave surface defines a concavity with a depth less than the height.

10. The endoprosthesis of claim 9, wherein the adhesion elements have a continuously decreasing diameter from the second end of the adhesion element to the first end.

11. The endoprosthesis of claim 1, wherein the adhesion elements are distributed along a longitudinal length and/or along a circumference of the cover with a gradient of spacing measured between centers of adjacent adhesion elements of 100 to 1000 μm.

12. The endoprosthesis of claim 1, wherein the oblique angle is being 30-75 degrees.

13. An endoprosthesis comprising:
a stent, wherein the stent has an inner surface defining a lumen, an outer surface, a first end, a second end, a thickness defined between the inner surface and the outer surface, and a plurality of openings extending through the thickness; and
a polymeric cover applied to the outer surface of the stent, the polymeric cover comprising a base and a plurality of outwardly extending adhesion elements arranged in a micropattern, wherein the base covers at least some of the plurality of openings of the stent;
wherein the adhesion elements are truncated cones with a circular outer wall, the adhesion elements extending radially outwardly from a first end of the adhesion elements at an outer surface of the base of the polymeric cover to a second end of the adhesion elements opposite the first end, the second end defining a concave surface, the adhesion elements having a first width at the first end and a second width at the second end, the second width being larger than the first width, wherein the circular outer wall has a continuously decreasing diameter from the second end to the first end;
wherein the combined truncated cone and concave end structure of the adhesion elements is configured to create a partial vacuum between the adhesion elements and a body lumen wall to adhere the endoprosthesis to the body lumen wall.

14. The endoprosthesis of claim 13, wherein the second width is 50 μm to 500 μm, a height measured from the first end to the second end is 20-50% of the second width, and the concave surface has a depth that is 10-20% of the second width.

15. The endoprosthesis of claim 13, wherein the adhesion elements are distributed along a longitudinal length and/or along a circumference of the cover with a gradient of spacing measured between centers of adjacent adhesion elements of 100 to 1000 μm.

16. The endoprosthesis of claim 13, wherein the micropattern is selected from the group consisting of a grid pattern; a rectangular array; a regular n-polygonal array; helical; and combinations thereof.

17. The endoprosthesis of claim 13, further comprising a retrieval element at a distal end of the endoprosthesis.

18. An endoprosthesis comprising:
a stent, wherein the stent has an inner surface defining a lumen, an outer surface, a first end, a second end, a thickness defined between the inner surface and the outer surface, and a plurality of openings extending through the thickness; and
a polymeric cover on the outer surface of the stent, the polymeric cover comprising a base and a plurality of adhesion elements arranged in a micropattern, wherein the base covers at least some of the plurality of openings of the stent;
wherein the adhesion elements are truncated cones with a circular outer wall, the adhesion elements extending radially outwardly from a first end of the adhesion elements at an outer surface of the base of the polymeric cover to a second end of the adhesion elements opposite the first end, the second end defining a concave surface, the adhesion elements having a first width at the first end and a second width at the second end, the second width being larger than the first width, wherein the adhesion elements are distributed along a longitudinal length and/or along a circumference of the cover with a gradient of spacing measured between centers of adjacent adhesion elements of 100 to 1000 pm;
wherein the combined truncated cone and concave end structure of the adhesion elements is configured to create a partial vacuum between the adhesion elements and a body lumen wall to adhere the endoprosthesis to the body lumen wall.

19. The endoprosthesis of claim 18, wherein the circular outer wall extends outward from the first end to the second end at an oblique angle relative to the outer surface of the base, wherein the second width is 50 μm to 500 μm, a height measured from the first end to the second end is 20-50% of the second width, and the concave surface has a depth that is 10-20% of the second width.

* * * * *